US012636244B2

(12) United States Patent
Hutton, III et al.

(10) Patent No.: US 12,636,244 B2
(45) Date of Patent: May 26, 2026

(54) PERSONAL CARE COMPOSITION CONTAINING A BIOSURFACTANT

(71) Applicant: The Procter & Gamble Company, Cincinnati, OH (US)

(72) Inventors: Howard David Hutton, III, Oregonia, OH (US); Isoken Omosefe Igwekala-Nweke, Springdale, OH (US); Dean Arthur Zimmerman, Liberty Township, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 283 days.

(21) Appl. No.: 18/495,792

(22) Filed: Oct. 27, 2023

(65) Prior Publication Data

US 2024/0156706 A1 May 16, 2024

Related U.S. Application Data

(60) Provisional application No. 63/420,767, filed on Oct. 31, 2022.

(51) Int. Cl.

*A61K 8/60* (2006.01)
*A61G 5/02* (2006.01)
*A61K 8/44* (2006.01)
*A61Q 5/02* (2006.01)

(52) U.S. Cl.

CPC ................ *A61K 8/604* (2013.01); *A61G 5/02* (2013.01); *A61K 8/442* (2013.01); *A61K 2800/596* (2013.01)

(58) Field of Classification Search

None

See application file for complete search history.

(56) References Cited

U.S. PATENT DOCUMENTS

| | | | |
|---|---|---|---|
| 8,563,490 | B2 | 10/2013 | Cox et al. |
| 9,271,908 | B2 | 3/2016 | Allef |
| 10,292,924 | B2 | 5/2019 | Schilling et al. |
| 2014/0095367 | A1 | 4/2014 | Ellis et al. |
| 2016/0081900 | A1 | 3/2016 | Cao et al. |
| 2017/0071835 | A1 | 3/2017 | Schelges et al. |
| 2017/0071836 | A1 | 3/2017 | Schelges et al. |
| 2017/0071837 | A1 | 3/2017 | Schelges et al. |
| 2020/0199492 | A1 | 6/2020 | Xue et al. |
| 2021/0185675 | A1 | 6/2021 | Shi |
| 2023/0320961 | A1 | 10/2023 | Igwekalanweke et al. |

FOREIGN PATENT DOCUMENTS

| | | | | |
|---|---|---|---|---|
| EP | 0499434 | A1 * | 8/1992 | ............ C11D 1/662 |
| EP | 2410039 | A1 | 1/2012 | |
| EP | 2786742 | A1 | 10/2014 | |
| EP | 2931237 | A1 | 10/2015 | |
| EP | 2931237 | B1 | 4/2018 | |
| EP | 2950778 | B1 | 11/2018 | |
| EP | 4023237 | A1 | 7/2022 | |
| JP | 2017501153 | A | 1/2017 | |
| JP | 2017137242 | A | 8/2017 | |
| WO | 2015091294 | A1 | 6/2015 | |
| WO | 2018071353 | A1 | 4/2018 | |
| WO | 2019219303 | A1 | 11/2019 | |
| WO | 2019243151 | A1 | 12/2019 | |
| WO | 2020016097 | A1 | 1/2020 | |
| WO | 2023016943 | A1 | 2/2023 | |

OTHER PUBLICATIONS

Buonocore,et al."Characterization of a New Mixture of Mono-Rhamnolipids Produced by Pseudomonas gessardii Isolated from Edmonson Point (Antarctica)", In Journal of Marine Drugs, vol. 18, Issue 5, May 20, 2020, pp. 1-18.

McMillan et al. "Sophorolipids in Personal Care Applications", An IP.com Prior Art Database Technical Disclosure, XP013193170, Apr. 6, 2022, 20 pages.

PCT Search Report and Written Opinion for PCT/US2023/077988 dated Feb. 12, 2024, 14 pages.

Seba George: "Microbial production of biosurfactants", Thesis, Nov. 1, 2010, pp. 1-291, XP055531605, Retrieved from the Internet: URL: http://shodhganga.inflibnet.ac.in:8080/jspui/handle/10603/25732 [retrieved on Dec. 7, 2018] the whole document.

Abdel-Mawgoud et al. "Rhamnolipids: diversity of structures, microbial origins and roles", Appl microbiology and biotechnology, vol. 86, Mar. 25, 2010, pp. 1323-1336.

Non-Final Office Action; U.S. Appl. No. 18/298,435, dated Jul. 23, 2025;See Patent Center.

* cited by examiner

*Primary Examiner* — Ali Soroush
*Assistant Examiner* — Elizabeth Anne Meyers
(74) *Attorney, Agent, or Firm* — Matthew J. Spegele; John Powell

(57) ABSTRACT

A sulfate-free personal care composition that includes a rhamnolipid surfactant and provides good cleaning and foaming properties. The rhamnolipid surfactant has a single rhamnose head group (i.e., mono-rhamno) and a single lipid tail group (i.e., mono lipid). The single lipid tail group has a carbon chain length of 10 to 13. The composition may include one or more additional surfactants selected from anionic surfactants, amphoteric surfactants, zwitterionic surfactants, non-ionic surfactants, cationic surfactants and combinations thereof, as long as the additional surfactant is free of sulfates. The composition also includes a dermatologically acceptable carrier.

16 Claims, 1 Drawing Sheet

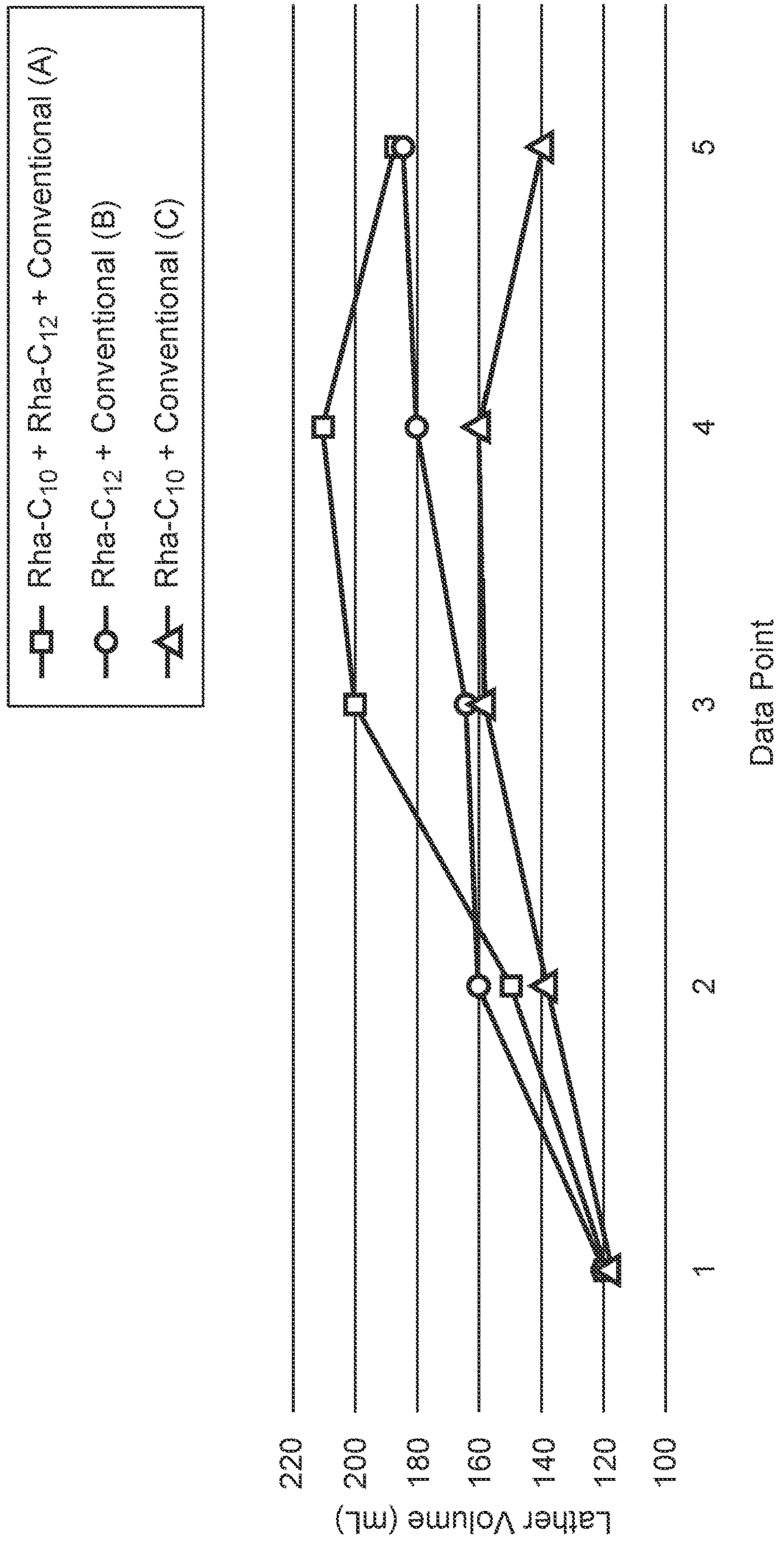
Rha-$C_{10}$ + Rha-$C_{12}$ + Conventional (A)
Rha-$C_{12}$ + Conventional (B)
Rha-$C_{10}$ + Conventional (C)
Lather Volume (mL)
220
200
180
160
140
120
100
1
2
3
4
5
Data Point

PERSONAL CARE COMPOSITION CONTAINING A BIOSURFACTANT

FIELD OF THE INVENTION

The present disclosure generally relates to a sulfate-free personal care composition comprising a glycolipid surfactant. More specifically, the present disclosure relates to sulfate-free personal care compositions comprising a surfactant with a single rhamnose head group and a single C10-C13 alkyl tail group.

BACKGROUND OF THE INVENTION

Human hair becomes soiled due to contact with the surrounding environment and from sebum secreted by the scalp. Soiled hair can have an undesirable feel and/or appearance. As a result, people may clean their hair with a shampoo composition that restores the hair to a clean and attractive appearance. Many conventional shampoos use sulfated surfactants such as sodium lauryl sulfate and/or sodium laureth sulfate to clean hair. Sulfated surfactants are generally very good at removing oil and other contaminants from hair, but they also have drawbacks. For example, sulfated surfactants are sometimes associated with poor quality hair feel, hair dryness and/or skin dryness after washing. This is commonly referred to as "harshness," and harsh shampoos generally face poor consumer acceptance.

Removing sulfated surfactants can provide a milder cleansing composition, but it has drawbacks, especially for conditioning shampoos (i.e., shampoos that provide a cleansing and conditioning benefit to hair). Conditioning shampoos with a sulfate-based surfactant system commonly use cationic conditioning polymers to form a coacervate with the sulfate-based surfactant during use, which provides the lathering/foaming properties desired by consumers. However, non-sulfated surfactants tend to be less effective at forming coacervates with the conditioning polymers as sulfated surfactants, which can lead to lackluster lathering, cleansing, and conditioning benefit. In addition, certain cationic conditioning polymers may introduce instability in products that use a sulfate-free surfactant system. In particular, a second phase known as surfactant-polymer coacervate can be formed in the composition (in situ coacervate), rather than forming during use as desired. Formation of an in situ coacervate is typically perceived by the consumer as an undesirable cloudy product or a product with a precipitated layer that has poor performance in use.

There is also a desire by consumers and manufacturers of cleansing composition for more environmentally friendly compositions. Surfactants used in conventional cleansing compositions are commonly derived from petrochemicals, which are generally perceived as environmentally unfriendly. Yet, sustainability in the use of cosmetic ingredients is becoming increasingly important and something that a growing number of consumers and manufacturers of cosmetic cleansing agents are demanding. The use of certain sustainable or naturally derived surfactants is known. Glycolipids are one such example of naturally derived surfactants.

Glycolipids are found in the cell membrane of eukaryotic organisms where they play a structural role as well as facilitating a number of other cellular functions. Glycolipid surfactants generally consist of a glycosyl head and lipid tail, which provides the amphiphilic behavior generally exhibited by a surfactant. However, naturally derived surfactants such as glycolipids may not provide the amount of foaming and cleaning performance desired by consumers. For example, U.S. Pat. No. 10,292,924 discloses a need for a cleansing composition containing a rhamnolipid that has good foam properties. The cleansing composition of U.S. Pat. No. 10,292,924 purportedly addresses this problem by providing a high concentration of di-rhamnolipids relative to mono-rhamnolipids.

In contrast, EP2410039 discloses a cleaning composition characterized by a ratio of mono-rhamnolipid to di-rhamnolipid of 95:5 to 45:55. EP2410039 also discloses that rhamnolipids are anionic surfactants that are sometimes mixed together to provide desirable foaming properties. In particular, E2410039 suggests that rhamnolipids with two shorter fatty acids are more active in reducing surface tension and as an emulsifier, and those rare rhamnolipids with a single fatty acid chain are not as effective. EP2410039 indicates that the main mono- and di-rhamnolipid components expressed by bacteria generally need to be extracted and reblended to provide suitable detergency. Thus, there is still a need for gentle cleansing compositions that provide desirable foam and cleansing properties using naturally derived surfactants.

Accordingly, it would be desirable to provide a personal cleansing composition that includes a naturally derived surfactant and exhibits desirable foaming and cleaning properties. It would also be desirable to provide such a composition that is free of sulfated surfactants. It would further be desirable to provide such a composition that exhibits good stability.

SUMMARY OF THE INVENTION

Disclosed herein is a personal care composition comprising a rhamnolipid surfactant selected from Rha-$C_{10}$, Rha-$C_{11}$, Rha-$C_{12}$, Rha-$C_{13}$ and combinations thereof; an additional surfactant selected from anionic surfactants, amphoteric surfactants, zwitterionic surfactants, non-ionic surfactants, cationic surfactants and combinations thereof; and a carrier. The personal care composition is free of sulfated surfactants.

BRIEF DESCRIPTION OF THE DRAWING

The FIGURE illustrates the foam height properties exhibited by various combinations of glycolipid surfactants.

DETAILED DESCRIPTION OF THE INVENTION

Shampoos containing sulfated surfactants are generally recognized as providing desirable cleansing properties, including sebum and soil removal and good lathering. However, sulfated surfactants are commonly perceived as being harsh. Replacing the sulfated surfactant(s) with a naturally derived surfactant, such as a glycolipid surfactant, may provide gentler cleansing, but may not provide a desired amount of foam and/or cleansing. Surprisingly, it has now been found that certain types of rhamnolipid surfactants can provide suitable foaming and cleansing. In particular, it has been discovered that certain mono-rhamno-mono-lipid surfactants provide better foaming and cleaning properties than conventional rhamnolipid surfactant congeners that have two or more lipid tail groups.

Reference within the specification to "embodiment(s)" or the like means that a particular material, feature, structure and/or characteristic described in connection with the embodiment is included in at least one embodiment, optionally, a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

All ingredient percentages described herein are by weight of the cosmetic composition, unless specifically stated otherwise, and may be designated as "wt %." All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges, and delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"About" modifies a particular value by referring to a range of plus or minus 20% or less of the stated value (e.g., plus or minus 15% or less, 10% or less, or even 5% or less).

"Apply" or "application," as used in reference to a composition, means to apply or spread the composition onto a human keratinous surface such as the skin or hair.

"Charge density" ("CD") means the ratio of positive charges on a polymer to the molecular weight of the polymer.

"Cleansing composition" refers to a personal care composition or product intended for use in cleaning a bodily surface such as skin or hair. Some non-limiting examples of cleansing compositions are shampoos, conditioners, conditioning shampoos, shower gels, liquid hand cleansers, facial cleansers, and the like.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration and food additives.

"Gel network phase" or "dispersed gel network phase" refers to a lamellar or vesicular solid crystalline phase that includes at least one fatty alcohol, at least one gel network surfactant, and a liquid carrier. The lamellar or vesicular phase can be formed of alternating layers with one layer including the fatty alcohol and the gel network surfactant and the other layer formed of the liquid carrier.

"Solid crystalline" refers to the crystalline structure of the lamellar or vesicular phase at ambient temperatures caused by the phase being below its melt transition temperature. For example, the melt transition temperature of the lamellar or vesicular phase may be about 30° C. or more (i.e., slightly above about room temperature). The melt transition temperature can be measured through differential scanning calorimetry, which is conventional measurement method known to those skilled in the art.

"Suitable for application to human hair" means that the personal care composition or components thereof, are acceptable for use in contact with human hair and the scalp and skin without undue toxicity, incompatibility, instability, allergic response, and the like.

"Substantially free of" means a composition or ingredient comprises less than 3% of a subject material, by weight of the composition or ingredient (e.g., less than 2%, less than 1% or even less than 0.5%). "Free of" means a composition or ingredient contains 0% of a subject material.

"Sulfated surfactants" means surfactants that contain a sulfate moiety. Some non-limiting examples of sulfated surfactants are sodium lauryl sulfate, sodium laureth sulfate, ammonium lauryl sulfate, and ammonium laureth sulfate. "Sulfate-free surfactant" refers to a surfactant that has no sulfate moieties.

Personal Care Composition

The sulfate-free personal care compositions herein include a mono-rhamno mono-lipid surfactant and, optionally, one or more additional non-sulfated surfactants and/or other ingredients commonly found in compositions of the type described. The personal care compositions herein may be provided in various product forms such as solutions, suspensions, shampoos, conditioners, lotions, creams, gels, toners, sticks, sprays, aerosols, ointments, cleansing liquid washes, solid bars, pastes, foams, mousses, shaving creams, wipes, strips, patches, hydrogels, film-forming products, facial and skin masks (with and without insoluble sheet), and the like. The composition form may follow from the particular dermatologically acceptable carrier chosen. In some aspects, the personal care compositions described herein may include a dispersed gel network phase that provides a milder, but effective, cleansing benefit to soiled hair in combination with a detersive glycolipid surfactant.

In some aspects, the compositions herein may contain less than 1% of an inorganic salt (e.g., 0% to 0.8%, 0.05% to 0.5%, or even 0.1% to 0.3%) such as sodium chloride, potassium chloride, sodium sulfate, ammonium chloride, sodium bromide, combinations of these and the like. In some conventional cleansing compositions, inorganic salt is added to thicken the product. However, in sulfate-free cleansing compositions, inorganic salt can introduce instability to the composition by aiding in the formation of a coacervate between anionic surfactants and cationic polymers which are commonly present. The coacervate typically has a gel-like consistency, and it can impact the rheological and performance properties of the composition as well as the consumer-perceived quality of the product.

By maintaining the desired salt concentration, it may be possible to reduce or eliminate product instability issues related to in situ coacervate formation. Accordingly, in some aspects, it can be important to avoid or minimize adding extra inorganic salt(s) as carryover ingredients (i.e., minor ingredients that may be present in another ingredient added to the composition). For example, commercially available sulfate-free surfactants such as glutamate-, betaine-, and sultaine-based surfactants typically comes with high levels of inorganic salt (e.g., 5% or higher). Product instability may manifest as a cloudy appearance, phase separation, and/or precipitation. Methods for determining the presence or absence of an in situ coacervate are known in the art, for example, as described in US 2023/0118201.

Of course, it is to be appreciated that when the cleansing composition is used as intended (i.e., diluted with water) it will form a coacervate to provide the desired cleaning benefit.

Rhamnolipid Surfactant

The personal care compositions described herein include one or more rhamnolipid biosurfactants to provide a foaming and cleaning benefit to personal care composition for cleaning a target bodily surface such as soiled hair and skin. The rhamnolipid surfactants herein may be produced by microorganisms (e.g., *Pseudomonas aeruginosa, Pseudomonas putida, Pseudomonas chlororaphis*). The rhamnolipid surfactant(s) facilitate cleaning due to their amphiphilic nature, which allows the surfactants to break up, and form micelles around, oil and other contaminants in the hair. The "entrapped" contaminant can then be rinsed off more easily with water. A description of various types of rhamnolipids is disclosed in EP2410039. Methods of making, extracting, and blending naturally produced rhamnolipids are known in the art.

The rhamnolipid surfactants used herein are mono-rhamnose mono-lipid surfactants in which the single lipid tail is between 10 and 13 carbon atoms long ("Rha-$C_{10-13}$"), for example, according to the formula illustrated below.

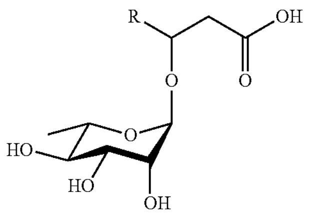

Where: R is an alkyl group with 10 to 13 carbon atoms.

Conventional wisdom dictates that rhamnolipids with a single lipid tail are generally unsuitable for use as surfactants due to, among other things, a low level of detergency, especially compared to conventional rhamnolipids that have two lipid tails. However, it has now been discovered that mono-rhamnolipids with a single fatty acid tail of between 10 and 13 carbons exhibit surprisingly good foaming and cleansing characteristics when added to a personal cleansing composition. Thus, the personal cleansing compositions herein may include 0.1% to 10% (e.g., 0.5% or even 1% to 5%) of a Rha-$C_{10-13}$ surfactant. In some aspects, the compositions herein may include additional surfactant(s). In such aspects, the Rha-$C_{10-13}$ surfactant may comprise 1% to 80% (e.g., 3% to 50%) of the total surfactant in the composition.

Additional Surfactants

The personal care compositions described herein may, optionally, include one or more additional non-sulfated surfactants. The additional surfactants may be selected from anionic surfactants such as isethionate, sarcosinate, sulfonate, sulfosuccinate, sulfoacetate, glycinate, glutamate, glucosecarboxylate, and phosphate ester surfactants; cationic surfactants such as polyquaternium surfactants; amphoteric/zwitterionic surfactants such as those surfactants broadly described as derivatives of aliphatic secondary and tertiary amines in which one of the aliphatic substituents contains from 8 to 18 carbon atoms and one aliphatic substituent contains an anionic group such as a carboxy, sulfonate, phosphate, or phosphonate group; non-ionic surfactants such as the polyethylene oxide condensates of alkyl phenols; and combinations of these. Some non-limiting examples of the optional surfactants described above are disclosed in US 20190105246, US 20180098923, U.S. Pat. No. 9,271,908, WO 2020/016097, and McCutcheon's Emulsifiers and Detergents, 2019, MC Publishing Co.

Some particularly suitable examples of additional surfactants include amphoteric surfactants such as cocoamphoacetates, cocoamphodiacetates, lauroamphoacetates, lauroamphodiacetates, amidobetaines, amidosulfobetaines, hydroxysultaines, and mixtures thereof and anionic surfactants such as isethionates, sarcosinates, sulfonates (e.g., alpha olefin sulfonates), taurates, alaninates, glycinates, glutamates, sulfosuccinates, and mixtures thereof).

The optional additional surfactants, when present, may be included in the personal care compositions to provide the desired cleaning and lather performance. Any additional surfactants should be physically and chemically compatible with the other components of the personal care compositions described herein and should not otherwise unduly impair product stability, aesthetics, or performance. In some aspects, additional surfactants may be present in the personal care compositions at 5% to 50% (e.g., 8% to 30%, 9% to 25%, or even 10% to 17%).

Dispersed Gel Network Phase

The personal care compositions described herein may include a dispersed gel network phase to provide a suitable cleaning benefit to the composition in combination with the detersive surfactant. A gel network phase can confer a cleaning benefit to the personal care composition through its hydrophobic nature. Specifically, it is believed, without being limited by theory, that the hydrophobic nature of the dispersed gel network allows the gel network to dissolve hydrophobic soils such as oil into the gel network. Once the soils are dissolved into the gel network, the gel network can be rinsed out of the hair or skin.

Suitable dispersed gel networks can be formed by combining a fatty alcohol and a gel network surfactant in a suitable ratio and heating the dispersion to a temperature above the melting point of the fatty alcohol. During the mixing process, the fatty alcohol melts allowing the gel network surfactant to partition and bring water into the fatty alcohol. Mixing of the gel network surfactant and fatty alcohols also changes the isotropic fatty alcohol drops into liquid crystalline phase drops. When the mixture is subsequently cooled below the melt transition temperature of the fatty alcohols, the liquid crystal phase is converted into a solid crystalline gel network. Additional details of suitable gel networks are described in G. M. Eccleston, "Functions of Mixed Emulsifiers and Emulsifying Waxes in Dermatological Lotions and Creams", *Colloids and Surfaces A: Physiochem. and Eng. Aspects* 123-124 (1997) 169-182; and by G. M Eccleston, "The Microstructure of Semisolid Creams", *Pharmacy International, Vol.* 7, 63-70 (1986), each of which is incorporated by reference herein.

In some aspects, it may be desirable to pre-form the gel network phase, which means that at least fifty percent of the mixture of the fatty alcohol, gel network surfactant, and liquid carrier are in a substantially solid crystalline phase prior to addition to the other components of the personal care composition. When the dispersed gel network is pre-formed, the gel network component can be prepared as a separate pre-mix, which, after being cooled, can be subsequently incorporated with a detersive surfactant and any other components of a personal care composition. While not intending to be limited by theory, it is believed that incorporation of a pre-formed gel network component with the detersive surfactant and other components of the personal care composition allows the formation of a substantially equilibrated lamellar dispersion ("ELD") in the final composition.

The ELD is a dispersed lamellar or vesicular phase resulting from the pre-formed gel network component substantially equilibrating with the detersive surfactants, carrier, and other optional components of a personal care composition. This equilibration occurs upon incorporation of the pre-formed gel network component with the other components of a personal care composition and can be effectively complete within about 24 hours after incorporation. The ELD does not form if the components which comprise the gel network component (i.e., the fatty alcohol, the gel network surfactant, and the liquid carrier) are added as individual components together with the other components of the personal care composition in one mixing step, and not as a separate pre-formed gel network component.

The presence of a gel network in the pre-mix and in a personal care composition can be confirmed by means known to one of skill in the art. For example, X-ray analysis, optical microscopy, electron microscopy, and differential scanning calorimetry can be used to identify a gel network. A suitable x-ray analysis is described in U.S. Patent App. Publication No. 2006/0024256 which is hereby incorporated by reference.

In some aspects, the scale size of the dispersed gel network in a personal care composition can range from about 10 nm to about 500 nm (e.g., 0.5 μm to 10 μm or 10 μm to about 150 m). The scale size distribution of the dispersed gel network in a personal care composition can be measured with a laser light scattering technique using a Horiba model LA 910 Laser Scattering Particle Size Distribution Analyzer (Horiba Instruments, Inc. Irvine California, USA). The scale size distribution in a personal care composition can be measured by combining 1.75 g of the personal care composition with 30 mL of 3% $NH_4Cl$, 20 mL of 2% $Na_2HPO_4 \cdot 7H_2O$, and 10 mL of 1% laureth-7 to form a mixture. This mixture is then stirred for 5 minutes. As appropriate for the individual Horiba instrument being used, samples in the range of 1 to 40 mL are taken and then injected into the Horiba instrument, which contains 75 mL of 3% $NH_4Cl$, 50 mL of 2% $Na_2HPO_4 \cdot 7H_2O$, and 25 mL of 1% laureth-7, until the Horiba instrument reading is between 88-92% T, which is needed for the scale size measurement. Once this is achieved, a measurement is taken after 2 minutes of circulation through the Horiba instrument to provide the scale size measurement. A subsequent measurement is taken using a sample of the personal care composition which has been heated above the melt transition temperature of all fatty materials present in the shampoo composition to ensure the dispersed gel network is melted. This subsequent measurement allows a scale size distribution to be taken of all the remaining materials in the personal care composition, which then can be compared to the scale size distribution of the first sample and assist in the analysis.

Gel Network Fatty Alcohol

The dispersed gel network may include a fatty alcohol (e.g., C10-C40 fatty alcohols) at 0.05% or more by weight of the composition (e.g., 0.05% to about 25%, 0.5% to 20%, or 1% to 8%). The fatty alcohol may be straight or branched chain and can be saturated or unsaturated. As can be appreciated, suitable fatty alcohols can be of natural, vegetable, or synthetic origin. In some aspects, it may be desirable to mix several fatty alcohols to provide a dispersed gel network phase with a melt transition temperature of about 38° C. or greater such as, for example, a mixture of cetyl alcohol and stearyl alcohol at a ratio of between 20:80 and 80:20. Some non-limiting examples of fatty alcohols that may be suitable for use herein include cetyl alcohol, stearyl alcohol, arachidyl alcohol, behenyl alcohol, $C_{21}$ fatty alcohol (1-heneicosanol), $C_{23}$ fatty alcohol (1-tricosanol), $C_{24}$ fatty alcohol (lignoceryl alcohol, 1-tetracosanol), $C_{26}$ fatty alcohol (1-hexacosanol), $C_{28}$ fatty alcohol (1-octacosanol), $C_{30}$ fatty alcohol (1-triacontanol), $C_{20-40}$ alcohols (e.g., Performacol® 350 and 425 Alcohols, available from New Phase Technologies), $C_{30-50}$ alcohols (e.g., Performacol® 550 Alcohol), $C_{40-60}$ alcohols (e.g., Performacol® 700 Alcohol), and mixtures thereof.

Gel Network Surfactant

The gel network phase may include a gel network surfactant at 0.01% to 15% by weight of the composition (e.g., 0.1% to about 10%, 0.2% to about 5%). The gel network surfactant is combined with the fatty alcohol and liquid carrier to form a gel network pre-mix, which can then be added to the other ingredients of the personal care composition.

In some aspects, the total weight of the gel network surfactant and the fatty alcohols is 0.5% to about 15% by weight of the personal care composition (e.g., 1% to 10%). In some aspects, the gel network surfactant may be included in the gel network at a desired weight ratio with respect to the fatty alcohols. For example, the ratio of the fatty alcohols to the gel network surfactant may be 1:5 to 100:1 (e.g., 1:1 to 40:1, 2:1 to 20:1, or even 3:1 to 10:1).

The gel network surfactant can be any suitable anionic, zwitterionic, amphoteric, cationic, and nonionic surfactants that is substantially free of sulfates. The detersive surfactant and the gel network surfactant can be independently selected and can be the same or different. In some aspects, the gel network surfactant has a hydrophobic tail group with a chain length of 10 to 40 carbon atoms. The hydrophobic tail group may be alkyl, alkenyl (containing up to 3 double bonds), alkyl aromatic, or branched alkyl. Mixtures of more than one gel network surfactant can also be used. Some non-limiting examples of gel network surfactants are disclosed in U.S. Patent App. Pub. No. 2006/0024256.

Liquid Carrier for the Gel Network Phase

In some aspects, the dispersed gel network phase may include a suitable liquid carrier at 0.05% to 95% by weight of the personal care composition. The liquid carrier can be water or another suitable solvent. The carrier and the gel network surfactant may be selected to work together to swell the fatty alcohol, which leads to the formation and stability of the gel network phase. A suitable solvent is any that can be used in the place of or in combination with water in the formation of the gel network phase. In some aspects, the liquid carrier can be substantially free of solvents other than water. In some aspects, the liquid carrier for the dispersed gel network phase can be included at a weight ratio of about 1:1 with the fatty alcohol of the dispersed gel network phase.

Carrier

The personal care compositions herein may include 20% to 95% of a liquid carrier (e.g., 60% to about 85%). The liquid carrier can separate from the liquid carrier of the dispersed gel network phase. The type and amount of liquid carrier should be selected to provide the composition with the desired rheological properties. The liquid carrier can be water or a miscible mixture of water and organic solvent. In some aspects, the liquid carrier can be water with little or no significant concentrations of organic solvent (e.g., less than 5%, 3%, 1%, 0.5% or even 0%). Suitable organic solvents can include water solutions of lower alkyl alcohols and polyhydric alcohols. Useful lower alkyl alcohols include monohydric alcohols having 1 to 6 carbons, such as ethanol and isopropanol. Exemplary polyhydric alcohols include propylene glycol, hexylene glycol, glycerin, and propane diol.

Other Optional Ingredients

The personal care compositions described herein may include a variety of optional ingredients to tailor the properties and characteristics of the composition, as desired. The optional ingredients may be well known materials that are commonly included in compositions of the type. The options ingredients should be physically and chemically compatible with the essential components of the personal care compositions and should not otherwise unduly impair the stability, aesthetics, or performance of the composition. Individual concentrations of optional components can generally range from about 0.001% to about 10%, by weight of a personal care composition.

Some non-limiting examples of other optional ingredients that can be included in the personal care compositions herein include: co-surfactants, deposition aids, cationic polymers, conditioning agents (including hydrocarbon oils, fatty esters, silicones), anti-dandruff agents, anti-microbial agents, suspending agents, viscosity modifiers, dyes, pigments, nonvolatile solvents or diluents (water soluble and insoluble), pearlescent aids, foam boosters, pediculocides, pH adjusting agents, perfumes, preservatives, chelants, proteins, vitamins, amino acids, skin active agents, sunscreens, UV absorbers, stabilizers, and combinations of these.

Multi-Phase Compositions

In some aspects, the personal care composition may be in the form of a multiphase composition. For example, a first phase of the composition may include traditional personal care components, such as structured surfactants, and a second phase may include a benefit phase. Methods of making multi-phase personal care compositions are disclosed in U.S. Pat. No. 8,653,014.

Method of Making a Personal Care Composition

The personal care composition described herein can be made using conventional methods for making compositions of the type desired (e.g., shampoo, conditioner or body wash). In some aspects, the composition may be made by: (a) combining a fatty alcohol, a gel network surfactant, and water at a temperature sufficient to allow partitioning of the secondary surfactant and the water into the fatty alcohol to form a pre-mix; (b) cooling the pre-mix below the chain melt temperature of the fatty alcohol to form a gel network; (c) adding the gel network to one or more detersive surfactants and a liquid carrier to form a personal care composition which includes a dispersed gel network phase having a melt transition temperature of at least about 38° C.

In some aspects, the gel network phase can be prepared by heating the fatty alcohol, the gel network surfactant, and water to a level in the range of about 75° C. to about 90° C. and mixing. This mixture can be cooled to 27-35° C. (e.g., by passing the mixture through a heat exchanger). As a result of this cooling step, at least about fifty percent of the mixture of the fatty alcohol and the gel network surfactant crystallize to form a crystalline gel network.

Other methods of preparing the gel network phase include sonication and/or milling of the fatty alcohol, the gel network surfactant, and water, while these components are heated, to reduce the particle size of the dispersed gel network phase. This results in an increase in surface area of the gel network phase, which allows the gel network surfactant and the water to swell the gel network phase. Another variation in preparing the gel network includes heating and mixing the fatty alcohol and the gel network surfactant first, and then adding that mixture to the water.

Method of Use

The personal care compositions described herein can be used in a conventional manner for cleansing and conditioning of hair or skin. Effective amounts of the composition for use generally range from 1 g to 50 g (e.g., 1 g to about 20 g). Generally, a method of treating hair or skin can include applying the personal care composition to the hair or skin. For example, an effective amount of the personal care composition can be applied to the hair or skin, which has been wetted with water, and then the composition can be rinsed off. Application to the hair typically includes working the composition through the hair such that most or all of the hair is contacted with the composition. The personal care composition can be used as a liquid solid, semi-solid, flake, gel, in a pressurized container with a propellant added, or used in a pump spray form. The viscosity of the product may be selected to accommodate the form desired.

In some aspects, the method for treating the hair or skin can include the steps of: (a) wetting the hair or skin with water; (b) applying an effective amount of the personal care composition to the hair or skin, and (c) rinsing the applied areas of skin or hair with water. These steps can be repeated as many times as desired to achieve the desired cleansing and conditioning benefit.

METHODS

Blender Lather Volume Method

This method can be used to evaluate a foam property that consumers associate with the quality of a shampoo product. This method is described in detail in Klein, Ken, "Evaluating Shampoo Foam," Cosmetic & Toiletries, Vol. 119, No. 10, p 32-35, 2004.

One (1) gram of the shampoo product is added to 39 grams of DI water at room temperature. This solution is carefully poured into a single-speed Magic Bullet MB1001 blender (or equivalent) to minimize the introduction of bubbles and agitated for 10 seconds. The foam is then poured into a 250 mL graduated cylinder, and the volume of the foam is measured and recorded. Optionally, after 3.5 minute, foam stability can be evaluated by recording the position of the foam/water interface (drainage). In this method, foam drainage describes the flow of liquid through the foam that occurs due to the weakening of the foam layer. Higher rates of foam drainage correspond to a less stable foam.

Lather Height and Creaminess Methods

The foaming potential of shampoos does not directly influence the physical behavior of hair fibers. However, shampoo foam can influence a user's perception or hair characteristics. In some instances, it may be helpful to distinguish lather from foam for shampoo evaluation. In particular, foam can generically refer to a mass of gas bubbles in a liquid film matrix, whereas lather more specifically refers to a type of foam formed during shampooing and other processes, wherein the foam consists of small bubbles that are densely packed, thus resisting flow.

This method provides a way to simulate the lather produced by surfactants when used on hair under typical shampooing conditions and quantify certain lather properties. Oil (e.g., sebum) and dirt are the two most common contaminates found on hair that can undesirably affect the lather properties of a shampoo. Thus, this method can be used to evaluate the effect of oil or dirt on lather properties.

Lather Height Oil Method and Lather Creaminess Method 100 mL of water (at 100° F.) is placed in a suitable blender (e.g., KitchenAid KSB560CU1 brand food mixer or equivalent), followed by 2 mL of the test composition and 1 mL of extra virgin olive oil. Blend the mixure on "stir" for 30 seconds and record the height of the lather in mm.

To assess creaminess, the lather is poured into a suitable bowl and is visually inspected. Based on the visual inspection, lather creaminess is rated from 0 to 5, where 0 is not at all creamy (bad) and 5 is the extremely creamy (good).

Lather Height Dirt Method 300 mL of water (at 100° F.) is placed in a suitable blender (e.g., KitchenAid KSB560CU1 brand food mixer or equivalent), followed by 3 mL of the test composition and 2 grams of potting soil (e.g., MIRACLE GRO brand potting soil or equivalent). Blend the mixture on "stir" for 15 seconds and record the height of the lather in mm.

Wet Hair In-Lab Screening (ILS) Method

This method can be used to determine the cleaning and/or conditioning properties of a hair care composition. In this method, a 20 g hair switch of Caucasian Low Lift Hair Tresses (International Hair Importers and Products, Inc.; Glendale, NY) is wetted with water, treated with test composition and placed in an ILS sink. The sink has a salon spray head/hose that is held in place but can be directed to run water over a hair tress that hangs from a rod placed over the sink. The tress can be moved in and out of the water as necessary. The water is maintained at a temperature of about 38° C. and a flow rate of about 5.7 liters per minute. The method is as follows:

Calibrate ILS sink to 38° C.

Hang the hair tress switch on rod in sink.

Wet hair tress thoroughly for 30 seconds. Squeegee the hair tress switch once using the index and middle fingers ("scissor fingers) from top to bottom to remove excess water. ("Squeegee" means to clamp the tress at the top in between your index and middle finger and stroke down once to remove water.)

Apply 0.1 g/g (product/hair) of the test composition to the front of the switch, from top to bottom.

Milk the hair tress switch for 15 seconds, then flip the bottom of the switch to the top and milk for another 15 seconds. "Milk" means to grab the top of the tress and stroke it downward while alternating hands to create lather.

Evaluate Slippery Feel at Application (within first 5 strokes). Start at the top just below the ponytail where the hair flattens out. Run fingers from top to bottom. Fingers may be slowed by the resistance versus skipping across the hair switch. Scale: 0=No Slip-10=Extremely Slippery.

Evaluate Lather Creaminess (look and feel, after 30 seconds of lathering). Scale: 0=No Creaminess-10=Extremely Creamy. Optionally, compare to Blender Lather Creaminess.

Evaluate Lather Combing (with lather still in switch). Using minimal pressure, place comb all the way through the hair (starting at the top) and using a minimal amount of force (comb from top to bottom) comb through hair switch. Scale: 0=hard to comb-10=easy to comb.

Rinse for 30 seconds (while lightly milking the switch).

Evaluate Slippery Feel While Rinsing (average rating throughout rinse). Scale: 0=No Slip-10=Extremely Slippery.

Squeegee the hair switch tress once with scissor fingers.

Evaluate Slippery Feel Post Rinsing. Squeegee once and assess feel. Scale: 0=No Slip-10=Extremely Slippery.

Evaluate Clean Feel Post Rinse. Stroke the hair from top to bottom between the thumb and two fingers with medium pressure. Gauge how clean or dirty the hair feels. Scale: 0=Low (Dirty)-10=High (Clean).

Evaluate Post Rinse Comb. Using the lowest pressure possible, placing comb (wide tooth side) all the way through the hair (front to back), and using a minimal amount of force (top to bottom) comb through hair switch. Scale: 0=Hard-10=Easy.

EXAMPLES

Example 1: Example Shampoo Formulations and Surfactant Performance

This example provides example formulations of the rhamnolipid surfactants herein and demonstrates their ability to provide suitable foaming and cleaning performance. The comparative and inventive compositions were tested for their ability to provide good lather volume, height and creaminess, which are well known shampoo properties. The shampoo properties summarized in Table 3 were measured according to the methods described above.

Table 1 provides five examples of comparative shampoo formulations (C1-C5) and 6 examples of inventive shampoo formulations (Inv 1-6). Comparative example 1 is a conventional sulfate-free shampoo composition that does not include a glycolipid surfactant. Comparative examples C2-C5 each include a commercially available di-rhamno-di-lipid surfactant mixture. Inventive examples 1-6 include a mono-rhamno-mono-lipid surfactant (Rha-$C_{10}$, Rha-$C_{11}$, Rha-$C_{12}$ or Rha-$C_{13}$). Inventive example 4 includes a mixture of Rha-$C_{10}$, Rha-$C_{12}$ and the di-rhamno di-lipid surfactant used in C2 and C3. The amount of rhamnolipid surfactant shown in Table 1 is the amount of active present in the composition.

The compositions in Table 1 can be made by adding DI water to a mixing vessel and heating to 75° C.±3° C. while agitating. For compositions C1, C2 and Inv 1, which contain sodium cocoyl isethionate (SCI) and/or sodium lauroyl sarcosinate (SLS), the anionic surfactant is added to the mixing vessel and mixed until fully dissolved (with no visible particles remaining and batch is clear). After the SCI and/or SLS have fully dissolved, the following materials can be added to the mixing vessel: sodium benzoate, tetrasodium EDTA, sodium salicylate, alkyl amidopropyl betaine, and rhamnolipids. The vessel contents are mixed for at least 10 minutes, and then cooled to less than 35° C. A polyquaternium-10 slurry is made with water, which is immediately added to the mixing vessel and mixed for 10 minutes. Perfume can be added and mixed in the mixture for at least 2 minutes. Sodium Hydroxide is used to titrate the mixture until the desired pH is reached. DI water is added to bring the final volume to 100%. The mixture is mixed for at least 10 minutes until homogeneity is achieved.

For the remaining compositions (i.e., C3-C5 and Inv 2-Inv 6), DI water is added to a mixing vessel and heated to 75° C.±3° C. while agitating. The following materials are then added to the mixing vessel: sodium benzoate, tetrasodium EDTA, sodium salicylate, alkyl amidopropyl betaine, and rhamnolipids. The vessel contents are mixed for at least 10 minutes. The batch is then cooled to less than 35° C. A polyquaternium-10 slurry is made with water, which is immediately added to the mixing vessel and mixed for 10 minutes. Perfume is then added and mixed in the mixture for at least 2 minutes. Sodium hydroxide is used to titrate the mixture until the desired pH is reached. DI water is added to bring the final volume to 100%. The mixture is mixed for at least 10 minutes until homogeneity is achieved.

TABLE 1

| Ingredient | C1 | C2 | Inv 1 | C3 | C4 | C5 | Inv 2 | Inv 3 | Inv 4 | Inv 5 | Inv 6 |
|---|---|---|---|---|---|---|---|---|---|---|---|
| Alkyl amidopropyl betaine | 9.8 | 9.8 | 9.8 | 9.8 | 9.8 | 9.8 | 9.8 | 9.8 | 9.8 | 9.8 | 9.8 |
| Sodium cocoyl isethionate | 6.0 | 6.0 | 6.0 | — | — | — | — | — | — | — | — |
| Sodium lauroyl sarcosinate | 2.5 | — | — | — | — | — | — | — | — | — | — |
| Di-lipid, Di-sugar rhamnolipid mixture I [1] | — | 0.6 | — | 8.5 | — | — | — | — | 2.1 | — | — |
| Di-lipid, Di-sugar rhamnolipid mixture II [2] | — | — | — | — | 8.5 | — | — | — | — | — | — |
| Di-lipid, Di-sugar rhamnolipid mixture III [3] | — | — | — | — | — | 8.5 | — | — | — | — | — |
| $Rha_1C_{10}$ tailored rhamnolipid [4] | — | — | — | — | — | — | 8.5 | — | 3.2 | — | — |
| $Rha_1C_{11}$ tailored rhamnolipid [4] | — | — | — | — | — | — | — | — | — | 8.5 | — |
| $Rha_1C_{12}$ tailored rhamnolipid [4] | — | — | 0.6 | — | — | — | — | 8.5 | 3.2 | — | — |
| $Rha_1C_{13}$ tailored rhamnolipid [4] | — | — | — | — | — | — | — | — | — | — | 8.5 |
| Polyquaternium-10 | 0.3 | 0.3 | 0.3 | 0.3 | 0.3 | 0.3 | 0.3 | 0.3 | 0.3 | 0.3 | 0.3 |
| Sodium Benzoate | 0.8 | 0.8 | 0.8 | 0.8 | 0.8 | 0.8 | 0.8 | 0.8 | 0.8 | 0.8 | 0.8 |
| Sodium salicylate | 0.5 | 0.5 | 0.5 | 0.5 | 0.5 | 0.5 | 0.5 | 0.5 | 0.5 | 0.5 | 0.5 |
| Tetrasodium EDTA | 0.2 | 0.2 | 0.2 | 0.2 | 0.2 | 0.2 | 0.2 | 0.2 | 0.2 | 0.2 | 0.2 |
| Perfume | 1.1 | 1.1 | 1.1 | 1.1 | 1.1 | 1.1 | 1.1 | 1.1 | 1.1 | 1.1 | 1.1 |
| Buffer | | pH 5.5 to 6.0 | | | | | | pH 6.8 to 7.2 | | | |
| Water | | | | | | | QS | | | | |
| Blender Foam Volume (No Soil) (mL) | 132 | 130 | 140* | 108 | 100 | 110 | 140* | 150* | 156* | 162* | 160* |
| Lather Blender Height (w/dirt) (mm) | 152 | 146 | 165* | 130 | 110 | 130 | 155* | 165* | 155* | 160* | 163* |
| Lather Blender Height (w/oil) (mm) | 83 | 76 | 76 | 25 | 20 | 25 | 70* | 100* | 55* | 80* | 85* |
| Lather Blender Creaminess Rating (0-5) | 4 | 5 | 5 | 0 | 0 | 0 | 4* | 4.5* | 3* | 4* | 4.5* |
| Slippery Feel at application | 8 | 7 | 9* | 6 | 6 | 6 | 5 | 9* | 9* | 7 | 7 |
| Lather Combing | 5 | 5 | 5 | 2 | — | — | 3 | 3 | 7* | 8* | 8* |
| Slippery Feel While Rinsing | 6 | 8 | 7 | 5 | 5 | 4 | 5 | 6 | 7* | 8* | 8* |
| Slippery Feel Post Rinsing | 5 | 7 | 7 | 3 | 2 | 3 | 4 | 5* | 5* | 7* | 6* |
| Ease of Combing | 7 | 8 | 5 | 2 | 1 | 1 | 2 | 4* | 4* | 5* | 9* |

[1] Rheance ® One brand rhamnolipids from Evonik (~50% active)
[2] Bio-RL1 ™ brand rhamnolipids from Wanhua Carfil (~38% active)
[3] ReNuva ™ RL-50 brand rhamnolipids from BioReNuva (~50% active)
[4] from GlycoSurf, Utah (~100% active)
*Significant difference vs. comparative example with conventional rhamnolipid surfactant As can be seen in Table 1, the inventive compositions performed better than the comparative compositions at both low surfactant level (0.6%) and high surfactant level (8.5%). Surprisingly, Inv 4, which contained a blend of conventional rhamnolipid surfactant and Rha-$C_{10}$ and Rha-$C_{12}$ performed better than the comparative examples and some of the other inventive examples.

Table 2 below provides prophetic examples of inventive compositions that include other sulfate-free surfactants. The compositions in Table 2 can be made using conventional processes, such as those described above.

TABLE 2

| Additional Examples | | | | | | | | |
|---|---|---|---|---|---|---|---|---|
| Ingredients | Ex. 5 | Ex. 6 | Ex. 7 | Ex. 8 | Ex. 9 | Ex. 10 | Ex. 11 | Ex. 12 |
| Alkyl amidopropyl betaine | 9.8 | | | | 9.8 | | | |
| Alkyl amphoacetate | | 9.8 | | | | 9.8 | | |
| Alkyl hydroxysultaine | | | 9.8 | | | | 9.8 | |
| Alkyl betaine | | | | 9.8 | | | | 9.8 |
| Acyl taurates | 3.0 | 7.0 | 3.0 | 5.0 | | | | |
| Acyl alaninate | | | | | | | | 5 |
| Rha-$C_{10}$ [2] | 5 | | | 3 | | | 8 | |
| Rha-$C_{11}$ [3] | | 1 | | | | 8 | | 3 |
| Rha-$C_{12}$ [4] | | | 5 | | 8 | | | |
| Sodium benzoate | 0.8 | 0.8 | 0.8 | 0.8 | 0.8 | 0.8 | 0.8 | 0.8 |
| Sodium salicylate | 0.5 | 0.5 | 0.5 | 0.5 | 0.5 | 0.5 | 0.5 | 0.5 |
| Tetrasodium EDTA | 0.2 | 0.2 | 0.2 | 0.2 | 0.2 | 0.2 | 0.2 | 0.2 |
| Polyquaternium-10 | 0.8 | 0.8 | 0.8 | 0.8 | 0.8 | 0.8 | 0.8 | 0.8 |
| Buffer | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 |
| DI Water | qs | qs | qs | qs | qs | qs | qs | qs |
| Ingredients | Ex. 13 | Ex. 14 | Ex. 15 | Ex. 16 | Ex. 17 | Ex. 18 | Ex. 19 | Ex. 20 |
| Alkyl amidopropyl betaine | 9.8 | | | | 9.8 | | | |
| Alkyl amphoacetate | | 9.8 | | | | 9.8 | | |
| Alkyl hydroxysultaine | | | 9.8 | | | | 9.8 | |
| Alkyl betaine | | | | 9.8 | | | | 9.8 |
| Acyl glutamate | 3.0 | 7.0 | 3.0 | 5.0 | | | | |
| Acyl glycinate | | | | | | | | 5 |

TABLE 2-continued

| Additional Examples | | | | | | | | |
|---|---|---|---|---|---|---|---|---|
| Rha-$C_{10}$ [2] | 5 | | | 3 | | | 8 | |
| Rha-$C_{11}$ [3] | | 1 | | | | 8 | | 3 |
| Rha-$C_{12}$ [4] | | | 5 | | 8 | | | |
| Sodium benzoate | 0.8 | 0.8 | 0.8 | 0.8 | 0.8 | 0.8 | 0.8 | 0.8 |
| Sodium salicylate | 0.5 | 0.5 | 0.5 | 0.5 | 0.5 | 0.5 | 0.5 | 0.5 |
| Tetrasodium EDTA | 0.2 | 0.2 | 0.2 | 0.2 | 0.2 | 0.2 | 0.2 | 0.2 |
| Polyquaternium-10 | 0.8 | 0.8 | 0.8 | 0.8 | 0.8 | 0.8 | 0.8 | 0.8 |
| Buffer | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 |
| DI Water | qs | qs | qs | qs | qs | qs | qs | qs |
| Ingredients | Ex. 21 | Ex. 22 | Ex. 23 | Ex. 24 | Ex. 25 | Ex. 26 | Ex. 27 | Ex. 28 |
| Alkyl amidopropyl betaine | 9.8 | | | | 9.8 | | | |
| Alkyl amphoacetate | | 9.8 | | | | 9.8 | | |
| Alkyl hydroxysultaine | | | 9.8 | | | | 9.8 | |
| Alkyl betaine | | | | 9.8 | | | | 9.8 |
| Acyl isethionate | 3.0 | 7.0 | 3.0 | 5.0 | | | | |
| Acyl sulfosuccinate | | | | | | | | 5 |
| Rha-$C_{10}$ [2] | 5 | | | 3 | | | 8 | |
| Rha-$C_{11}$ [3] | | 1 | | | | 8 | | 3 |
| Rha-$C_{12}$ [4] | | | 5 | | 8 | | | |
| Sodium benzoate | 0.8 | 0.8 | 0.8 | 0.8 | 0.8 | 0.8 | 0.8 | 0.8 |
| Sodium salicylate | 0.5 | 0.5 | 0.5 | 0.5 | 0.5 | 0.5 | 0.5 | 0.5 |
| Tetrasodium EDTA | 0.2 | 0.2 | 0.2 | 0.2 | 0.2 | 0.2 | 0.2 | 0.2 |
| Polyquaternium-10 | 0.8 | 0.8 | 0.8 | 0.8 | 0.8 | 0.8 | 0.8 | 0.8 |
| Buffer | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 |
| DI Water | qs | qs | qs | qs | qs | qs | qs | qs |
| Ingredients | Ex. 29 | Ex. 30 | Ex. 31 | Ex. 32 | Ex. 33 | Ex. 34 | Ex. 35 | Ex. 36 |
| Alkyl amidopropyl betaine | 9.8 | | | | 9.8 | | | |
| Alkyl amphoacetate | | 9.8 | | | | 9.8 | | |
| Alkyl hydroxysultaine | | | 9.8 | | | | 9.8 | |
| Alkyl betaine | | | | 9.8 | | | | 9.8 |
| Acyl methyl isethionate | 3.0 | 7.0 | 3.0 | 5.0 | | | | |
| $C_{14-16}$ alpha olefin sulfonate | | | | | | | | 5 |
| Rha-$C_{10}$ [2] | 5 | | | 3 | | | 8 | |
| Rha-$C_{11}$ [3] | | 1 | | | | 8 | | 3 |
| Rha-$C_{12}$ [4] | | | 5 | | 8 | | | |
| Sodium benzoate | 0.8 | 0.8 | 0.8 | 0.8 | 0.8 | 0.8 | 0.8 | 0.8 |
| Sodium salicylate | 0.5 | 0.5 | 0.5 | 0.5 | 0.5 | 0.5 | 0.5 | 0.5 |
| Tetrasodium EDTA | 0.2 | 0.2 | 0.2 | 0.2 | 0.2 | 0.2 | 0.2 | 0.2 |
| Polyquaternium-10 | 0.8 | 0.8 | 0.8 | 0.8 | 0.8 | 0.8 | 0.8 | 0.8 |
| Buffer | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 | To pH 6.8 to 7.2 |
| DI Water | qs | qs | qs | qs | qs | qs | qs | qs |

[1] RHEANCE ONE brand glycolipid surfactant from Evonik (~50% active).
[2] Rha-C10 from GlycoSurf, Utah (~100% active).
[3] Rha-C11 from GlycoSurf, Utah (~100% active).
[4] Rha-C12 from GlycoSurf, Utah (~100% active).

Example 3: Lather Synergy

This example demonstrates the unexpected lather volume synergy exhibited by a shampoo that contains a mixture of a Rha-$C_{10}$ surfactant, Rha-$C_{12}$ surfactant and a conventional rhamnolipid surfactant. Because Rha-$C_{10}$ and Rha-$C_{12}$ surfactants are generally not desired for use in conventional shampoos they tend to be treated as specialty ingredients, which are more expensive than conventional glycolipid surfactants. Thus, mixing Rha-$C_{10}$ and Rha-$C_{12}$ surfactants with conventional glycolipid surfactants can reduce the manufacturing costs of the shampoo and provide superior lather volume.

This example tests three legs of compositions (A-C) that have varying levels of Rha-$C_{10}$, Rha-$C_{12}$, and conventional glycolipid surfactant (RHEANCE ONE from Evonik). The test compositions are simple solutions of water and surfactant. Lather volume was measured according to the Lather Volume method described above. The Lather Volume recorded for each data point is summarized in Table 3 and illustrated in the FIGURE.

TABLE 3

| Lather Volume | | |
|---|---|---|
| Composition | Data point description | Lather Volume (mL) |
| A | 1 = 100% Conventional | 120 |
| | 2 = 12.5% Rha-$C_{10}$, 12.5% Rha-$C_{12}$, 75% Conventional | 150 |
| | 3 = 25% Rha-$C_{10}$, 25% Rha-$C_{12}$, 50% Conventional | 200 |
| | 4 = 37.5% Rha-$C_{10}$, 37.5% Rha-$C_{12}$, 25% Conventional | 210 |
| | 5 = 50% Rha-$C_{10}$, 50% Rha-$C_{12}$ | 187 |

TABLE 3-continued

| Lather Volume | | |
|---|---|---|
| Composition | Data point description | Lather Volume (mL) |
| B | 1 = 100% Conventional | 120 |
| | 2 = 25% Rha-$C_{12}$, 75% Conventional | 160 |
| | 3 = 50% Rha-$C_{12}$, 50% Conventional | 164 |
| | 4 = 75% Rha-$C_{12}$, 25% Conventional | 180 |
| | 5 = 100% Rha-$C_{12}$ | 184 |
| C | 1 = 100% Conventional | 120 |
| | 2 = 25% Rha-$C_{10}$, 75% Conventional | 140 |
| | 3 = 50% Rha-$C_{10}$, 50% Conventional | 160 |
| | 4 = 75% Rha-$C_{10}$, 25% Conventional | 160 |
| | 5 = 100% Rha-$C_{10}$ | 141 |

As can be seen in Table 3 and the FIGURE, the combination of Rha-$C_{10}$, Rha-$C_{12}$, and conventional glycolipid surfactant in composition A provided unexpectedly better Lather Volume than compositions B and C. In particular, composition A provided appeared to provide unexpectedly better Lather Volume when the ratio of Rha-$C_{10}$ to Rha-$C_{12}$ is 1:1 and the ratio of Rha-$C_{10}$+Rha-$C_{12}$ to conventional rhamnolipid or Rha-$C_{12}$ alone is between 1:3 and 1:0.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A surfactant system, comprising:

a rhamnolipid surfactant comprising a mono-rhamno-mono-lipid surfactant selected from Rha-$C_{10}$, Rha-$C_{11}$, Rha-$C_{12}$, Rha-$C_{13}$ and combinations thereof; and di-rhamno-di-lipid surfactant an additional surfactant selected from anionic surfactants, amphoteric surfactants, zwitterionic surfactants, nonionic surfactants, cationic surfactants and combinations thereof, wherein the additional surfactant is free of sulfates;

wherein the rhamnolipid surfactant comprises about 25% to about 75%, by weight of the rhamnolipid surfactant, of the mono-rhamno-mono-lipid surfactant and about 25% to about 75%, by weight of the rhamnolipid surfactant, of the di-rhamno di-lipid surfactant, wherein the combination of mono-rhamno mono-lipid surfactant and di-rhamno di-lipid surfactant exhibit a synergistic Lather Volume according to the Foam Drainage method.

2. The surfactant system of claim 1, wherein the mono-rhamno-mono-lipid surfactant comprises a Rha-$C_{10}$ surfactant and a Rha-$C_{12}$ surfactant.

3. The surfactant system of claim 2, wherein the Rha-$C_{10}$ surfactant and Rha-$C_{12}$ surfactant are present at a weight ratio of Rha-$C_{10}$ to Rha-$C_{12}$ of about 1:10 to about 10:1.

4. The surfactant system of claim 1, wherein the additional surfactant is selected from cocoamphoacetates, cocoamphodiacetates, lauroamphoacetates, lauroamphodiacetates, amidobetaines, amidosulfobetaines, hydroxysultaines, isethionates, sarcosinates, sulfonates, taurates, alaninates, glycinates, glutamates, sulfosuccinates, and mixtures thereof.

5. A personal care composition, comprising:

a) the surfactant system of claim 1; and b) a dermatologically acceptable carrier.

6. The personal care composition of claim 5, wherein the composition exhibits a Lather Height of at least about 50 mm according to Lather Height Oil Method.

7. The personal care composition of claim 5, wherein the composition exhibits a Lather Height of at least about 150 mm according to Lather Height Dirt Method.

8. The personal care composition of claim 5, further comprising less than about 1%, by weight of the personal care composition, inorganic salt.

9. The personal care composition of claim 5, further comprising a dispersed gel network.

10. The personal care composition of claim 9, wherein the gel network comprises a fatty alcohol, a gel network surfactant, and a liquid carrier, and wherein the fatty alcohol is in the form of liquid crystal drops.

11. The personal care composition of claim 9, wherein the dispersed gel network comprises about 0.05 wt % or more of a fatty alcohol and about 0.01 wt % or more of a gel network surfactant selected from anionic surfactants, cationic surfactants, zwitterionic surfactants, non-ionic surfactants, and mixtures thereof.

12. The personal care composition of claim 5, further comprising a cationic polymer.

13. The personal care composition of claim 5, wherein the mono-rhamno-mono-lipid system comprises a Rha-$C_{10}$ surfactant and a Rha-$C_{12}$ surfactant.

14. The personal care composition of claim 13, wherein the Rha-$C_{10}$ surfactant and Rha-$C_{12}$ surfactant are present at a weight ratio of Rha-$C_{10}$ to Rha-$C_{12}$ of about 5:1 to 1:5.

15. The personal care composition of claim 13, wherein the Rha-$C_{10}$ surfactant and Rha-$C_{12}$ surfactant are about 1 wt % to about 80 wt % of the total surfactants in the personal care composition.

16. A method of cleaning a target body surface, comprising:

wetting the target body surface with water;

applying about 1 to about 50 g of the personal care composition of claim 6 to the wetted body surface;

working the composition on the wetted bodily surface to produce a lather; and rinsing the composition from the target body surface with water.

* * * * *